(12) United States Patent
Artemiadis et al.

(10) Patent No.: US 9,707,442 B2
(45) Date of Patent: Jul. 18, 2017

(54) SYSTEMS AND METHODS FOR GAIT REHABILITATION USING MECHANICAL PERTURBATIONS

(71) Applicant: ARIZONA BOARD OF REGENTS ON BEHALF OF ARIZONA STATE UNIVERSITY, Tempe, AZ (US)

(72) Inventors: Panagiotis Artemiadis, Tempe, AZ (US); Jeffrey Skidmore, Tempe, AZ (US)

(73) Assignee: Arizona Board of Regents on behalf of Arizona State University, Tempe, AZ (US)

( * ) Notice: Subject to any disclaimer, the term of this patent is extended or adjusted under 35 U.S.C. 154(b) by 0 days.

(21) Appl. No.: 15/001,742

(22) Filed: Jan. 20, 2016

(65) Prior Publication Data

US 2016/0144226 A1    May 26, 2016

Related U.S. Application Data

(63) Continuation-in-part of application No. PCT/US2014/062534, filed on Oct. 28, 2014.

(60) Provisional application No. 62/105,473, filed on Jan. 20, 2015, provisional application No. 61/896,509, filed on Oct. 28, 2013.

(51) Int. Cl.
| | |
|---|---|
| A63B 22/00 | (2006.01) |
| A63B 22/02 | (2006.01) |
| A63B 69/00 | (2006.01) |
| A61B 5/11 | (2006.01) |

(52) U.S. Cl.
CPC ...... *A63B 22/0292* (2015.10); *A63B 22/0046* (2013.01); *A63B 22/0228* (2015.10); *A61B 5/112* (2013.01); *A63B 69/0064* (2013.01); *A63B 2022/0094* (2013.01); *A63B 2220/806* (2013.01); *A63B 2225/50* (2013.01); *A63B 2230/01* (2013.01); *A63B 2230/605* (2013.01)

(58) Field of Classification Search
USPC ................ 482/54; 601/23, 27, 35
See application file for complete search history.

(56) References Cited

U.S. PATENT DOCUMENTS

| | | | | |
|---|---|---|---|---|
| 5,302,162 | A * | 4/1994 | Pasero | A63B 22/02 198/814 |
| 8,246,354 | B2 * | 8/2012 | Chu | A63B 22/0292 434/258 |
| 8,262,590 | B2 * | 9/2012 | Padula | A61B 5/1038 600/592 |
| 2010/0056960 | A1 * | 3/2010 | Lanny | A61B 5/1038 600/592 |

(Continued)

OTHER PUBLICATIONS

Jeffrey Skidmore, Andrew Barkan and Panagiotis Artemiadis, "Investigation of Contralateral Leg Response to Unilateral Stiffness Perturbations using a Novel Device," IEEE/RSJ International Conference on Intelligent Robots and Systems (IROS), 2014.

(Continued)

*Primary Examiner* — Stephen Crow
(74) *Attorney, Agent, or Firm* — Ari M. Bai; Polsinelli PC

(57) ABSTRACT

Embodiments for systems and methods of a variable stiffness treadmill for gait rehabilitation using mechanical perturbations on the unimpaired leg to provide therapy to the impaired leg are disclosed.

18 Claims, 10 Drawing Sheets

(56) References Cited

U.S. PATENT DOCUMENTS

| | | | | |
|---|---|---|---|---|
| 2014/0100491 A1* | 4/2014 | Hu | ............... | A61H 3/008 601/27 |
| 2016/0144226 A1* | 5/2016 | Artemiadis | ........ | A63B 22/0228 482/54 |
| 2016/0243397 A1* | 8/2016 | Artemiadis | ........ | A63B 69/0064 |

OTHER PUBLICATIONS

Jeffrey Skidmore and Panagiotis Artemiadis, "Unilateral Floor Stiffness Perturbations Systematically Evoke Contralateral Leg Muscle Responses: a New Approach to Robotassisted Gait Therapy," IEEE Transactions on Neural Systems and Rehabilitation Engineering. (submitted on Oct. 2014).

R. af Klint, N. Mazzaro, J. B. Nielsen, T. Sinkjaer, and M. J. Grey, "Load rather than length sensitive feedback contributes to soleus muscle activity during human treadmill walking," Journal of neurophysiology, vol. 103, No. 5, pp. 2747-2756, 2010.

M. J. Stephens and J. F. Yang, "Loading during the stance phase of walking in humans increases the extensor emg amplitude but does not change the duration of the step cycle," Experimental Brain Research, vol. 124, No. 3, pp. 363370,1999.

J. F. Yang, M. J. Stephens, and R. Vishram, "Transient disturbances to one limb produce coordinated, bilateral responses during infant stepping," Journal of neurophysiology, vol. 79, No. 5, pp. 2329-2337, 1998.

V. Dietz, R. Muller, and G. Colombo, "Locomotor activity in spinal man: significance of afferent input from joint and load receptors," Brain, vol. 125, No. 12, pp. 2626-2634, 2002.

V. Dietz and J. Duysens, "Significance of load receptor input during locomotion: a review," Gait & posture, vol. 11, No. 2, pp. 102-110, 2000.

M. Faist, C. Hoefer, M. Hodapp, V. Dietz, W. Berger, and J. Duysens, "In humans ib facilitation depends on locomotion while suppression of ib inhibition requires loading," Brain research, vol. 1076, No. 1, pp. 87-92, 2006.

Y. P. Ivanenko, R. Grasso, V. Macellari, and F. Lacquaniti, "Control of foot trajectory in human locomotion: role of ground contact forces in simulated reduced gravity," J. Neurophysiol., vol. 87, pp. 3070-3089, 2002.

M. J. Grey, J. B. Nielsen, N. Mazzaro, and T. Sinkjr, "Positive force feedback in human walking," The Journal of physiology, vol. 581, No. 1, pp. 99-105, 2007.

R. af Klint, J. B. Nielsen, T. Sinkjaer, and M. J. Grey, "Sudden drop in ground support produces force-related unload response in human overground walking," Journal of neurophysiology, vol. 101, No. 4, pp. 1705-1712, 2009.

D. S. Marigold and A. E. Patla, "Adapting locomotion to different surface compliances: neuromuscular responses and changes in movement dynamics," Journal of neurophysiology, vol. 94, No. 3, pp. 1733-1750, 2005.

K. Nakazawa, N. Kawashima, M. Akai, and H. Yano, "On the reflex coactivation of ankle flexor and extensor muscles induced by a sudden drop of support surface during walking in humans," Journal of Applied Physiology, vol. 96, No. 2, pp. 604-611, 2004.

M. H. van der Linden, D. S. Marigold, F. J. M. Gabreels, and J. Duysens, "Muscle reflexes and synergies triggered by an unexpected support surface height during walking," Journal of neurophysiology, vol. 97, No. 5, pp. 3639-3650, 2007.

W. Berger, V. Dietz, and J. Quintern, "Corrective reactions to stumbling in man: neuronal coordination of bilateral leg muscle activity during gait," Journal of physiology, vol. 357, pp. 109-125, 1984.

T. Lam, C. Wolstenholme, M. Linden, M. Y. C. Pang, and J. F. Yang, "Stumbling Corrective Responses During Treadmill Elicited Stepping in Human Infants," The Journal of physiology, vol. 553, No. 1, pp. 319-331, 2003.

K. Boyer, Changes in muscle activity in response to different impact forces affect soft tissue compartment mechanical properties. Journal of biomechanical engineering, 2007.

T. Klarner, "Contribution of load and length related manipulations to muscle responses during force perturbations," MS Thesis, University of British Columbia, 2010.

T. Sinkjaer, J. B. Andersen, M. Ladouceur, L. O. D. Christensen, and J. B. Nielsen, "Major role for sensory feedback in soleus EMG activity in the stance phase of walking in man," The Journal of physiology, vol. 523, No. 3, pp. 817-827, 2000.

M. J. MacLellan and A. E. Patla, "Adaptations of walking pattern on a compliant surface to regulate dynamic stability," Experimental brain research, vol. 173, No. 3, pp. 521-530, 2006.

M. D. Chang, E. Sejdrc, V. Wright, and T. Chau, "Measures of dynamic stability: detecting differences between walking overground and on a compliant surface," Human movement science, vol. 29, No. 6, pp. 977-986, 2010.

A. E. Kerdok, A. A. Biewener, T. A. McMahon, P. G. Weyand, and H. M. Herr, "Energetics and mechanics of human running on surfaces of different stiffnesses," Journal of Applied Physiology, vol. 92, No. 2, pp. 469-478, 2002.

T. A. McMahon and P. R. Greene, "The influence of track compliance on running," Journal of biomechanics, vol. 12, No. 12, pp. 893-904, 1979.

A. Jafari, N. G. Tsagarakis, and D. G. Caldwell, "AwAS-II: A new Actuator with Adjustable Stiffness based on the novel principle of adaptable pivot point and variable lever ratio," in Robotics and Automation (ICRA), 2011 IEEE International Conference on, 2011, pp. 4638-4643.

A. Barkan, J. Skidmore, and P. Artemiadis, "Variable Stiffness Treadmill (VST): a Novel Tool for the Investigation of Gait,". IEEE Intern. Confer. on Robotics and Automation (ICRA), 2014.

R. C. Browning, E. A. Baker, J. A. Herron, and R. Kram, "Effects of obesity and sex on the energetic cost and preferred speed of walking," Journal of Applied Physiology, vol. 100, No. 2, pp. 390-398, 2006.

R. V. Levine and A. Norenzayan, "The pace of life in 31 countries," Journal of cross-cultural psychology, vol. 30, No. 2, pp. 178-205, 1999.

R. M. Pawar and M. N. Pawar, "Foot length—a functional parameter for assessment of height," The Foot, vol. 22, No. 1, pp. 31-34, 2012.

C. T. Farley, H. H. Houdijk, C. Van Strien, and M. Louie, "Mechanism of leg stiffness adjustment for hopping on surfaces of different stiffnesses," Journal of Applied Physiology, vol. 85, No. 3, pp. 1044-1055, 1998.

D. P. Ferris and C. T. Farley, "Interaction of leg stiffness and surface stiffness during human hopping," Journal of applied physiology, vol. 82, No. 1, pp. 15-22, 1997.

D. P. Ferris, K. Liang, and C. T. Farley, "Runners adjust leg stiffness for their first step on a new running surface," Journal of biomechanics, vol. 32, No. 8, pp. 787-794, 1999.

S. Grillner, "The motor infrastructure: from ion channels to neuronal networks," Nature Reviews Neuroscience, vol. 4, No. 7, pp. 573-586, 2003.

P. Langhorne, J. Bernhardt, and G. Kwakkel, "Stroke rehabilitation," The Lancet, vol. 377, No. 9778, pp. 1693-1702, 2011.

S. Barker-Collo, V. Feigin, V. Parag, C. Lawes, and H. Senior, "Auckland stroke outcomes study part 2: Cognition and functional outcomes 5 years poststroke," Neurology, vol. 75, No. 18, pp. 1608-1616, 2010.

M. Pekna, M. Pekny, and M. Nilsson, "Modulation of neural plasticity as a basis for stroke rehabilitation," Stroke, vol. 43, No. 10, pp. 2819-2828, 2012.

S. Jezernik, G. Colombo, T. Keller, H. Frueh, and M. Morari, "Robotic orthosis lokomat: A rehabilitation and research tool," Neuromodulation Technology at the neural interface, vol. 6, No. 2, pp. 108-115, 2003.

S. Hesse, D. Uhlenbrock et al., "A mechanized gait trainer for restoration of gait," Journal of rehabilitation research and development, vol. 37, No. 6, pp. 701-708, 2000.

J. F. Veneman, R. Kruidhof, E. E. Hekman, R. Ekkelenkamp, E. H. Van Asseldonk, and H. Van Der Kooij, "Design and evaluation of

(56) References Cited

OTHER PUBLICATIONS the lopes exoskeleton robot for interactive gait rehabilitation," Neural Systems and Rehabilitation Engineering, IEEE Transactions on, vol. 15, No. 3, pp. 379-386, 2007.

A. Morbi, M. Ahmadi, and a. Nativ, "GaitEnable: An omnidirectional robotic system for gait rehabilitation," in Mechatronics and Automation (ICMA), 2012 International Conference on. IEEE, 2012, pp. 936-941.

S. K. Banala, S. K. Agrawal, and J. P. Scholz, "Active leg exoskeleton (alex) for gait rehabilitation of motor-impaired patients," In Rehabilitation Robotics, 2007. ICORR 2007. IEEE 10th International Conference on. IEEE, 2007, pp. 401-407.

M. Peshkin, D. A. Brown, J. J. Santos-Munn'e, A. Makhlin, E. Lewis, J. E. Colgate, J. Patton, and D. Schwandt, "Kineassist: A robotic overground gait and balance training device," in Rehabilitation Robotics, 2005. ICORR 2005. 9th International Conference on. IEEE, 2005, pp. 241-246.

A. Mayr, M. Kofler, E. Quirbach, H. Matzak, K. Frohlich, and L. Saltuari, "Prospective, blinded, randomized crossover study of gait rehabilitation in stroke patients using the lokomat gait orthosis," Neurorehabilitation and Neural Repair, vol. 21, No. 4, pp. 307-314, 2007.

M. Pohl, C. Werner, M. Holzgraefe, G. Kroczek, I. Wingendorf, G. Hoolig, R. Koch, and S. Hesse, "Repetitive locomotor training and physiotherapy improve walking and basic activities of daily living after stroke: a single-blind, randomized multicentre trial (deutsche gangtrainerstudie, degas)," Clinical Rehabilitation, vol. 21, No. 1, pp. 17-27, 2007.

J. Hidler, D. Nichols, M. Pelliccio, K. Brady, D. D. Campbell, J. H. Kahn, and T. G. Hornby, "Multicenter randomized clinical trial evaluating the effectiveness of the lokomat in subacute stroke," Neurorehabilitation and Neural Repair, vol. 23, No. 1, pp. 5-13, 2009.

T. G. Hornby, D. D. Campbell, J. H. Kahn, T. Demott, J. L. Moore, and H. R. Roth, "Enhanced gait-related improvements after therapistversus robotic-assisted locomotor training in subjects with chronic stroke a randomized controlled study," Stroke, vol. 39, No. 6, pp. 1786-1792, 2008.

W. H. Chang and Y.-H. Kim, "Robot-assisted therapy in stroke rehabilitation," Journal of Stroke, vol. 15, No. 3, pp. 174-181, 2013.

M. H. van der Linden, D. S. Marigold, F. J. Gabreels, and J. Duysens, "Muscle reflexes and synergies triggered by an unexpected support surface height during walking," Journal of neurophysiology, vol. 97, No. 5, pp. 3639-3650, 2007.

V. Dietz, W. Zijlstra, and J. Duysens, "Human neuronal interlimb coordination during split-belt locomotion," Experimental brain research, vol. 101, No. 3, pp. 513-520, 1994.

J. Skidmore, A. Barkan, and P. Artemiadis, "Variable Stiffness Treadmill (VST): System Development, Characterization and Preliminary Experiments," IEEE/ASME Transactions on Mechatronics, 2014.

P. K. Artemiadis and H. I. Krebs, "Interlimb coordination evoked by unilateral mechanical perturbation during body-weight supported gait," In Proc. Of IEEE 12th International Conference on Rehabilitation Robotics, 2011.

S. Rossignol, R. Debuck, and J.-P. Gossard, "Dynamic sensorimotor interactions in locomotion," Physiological reviews, vol. 10, No. 1152, pp. 86-89, 2006.

L. O. Christensen, N. Petersen, J. B. Andersen, T. Sinkjr, and J. B. Nielsen, "Evidence for transcortical reflex pathways in the lower limb of man," Progress in neurobiology, vol. 62, No. 3, pp. 251-272, 2000.

U. Bogataj, N. Gros, M. Kljaji'c, R. A'cimovi'c, and M. Male zi c, "The rehabilitation of gait in patients with hemiplegia: a comparison between conventional therapy and multichannel functional electrical stimulation therapy," Physical Therapy, vol. 75, No. 6, pp. 490-502, 1995.

P. H. Peckham and J. S. Knutson, "Functional electrical stimulation for neuromuscular applications," Annu. Rev. Biomed. Eng., vol. 7, pp. 327-360, 2005.

\* cited by examiner

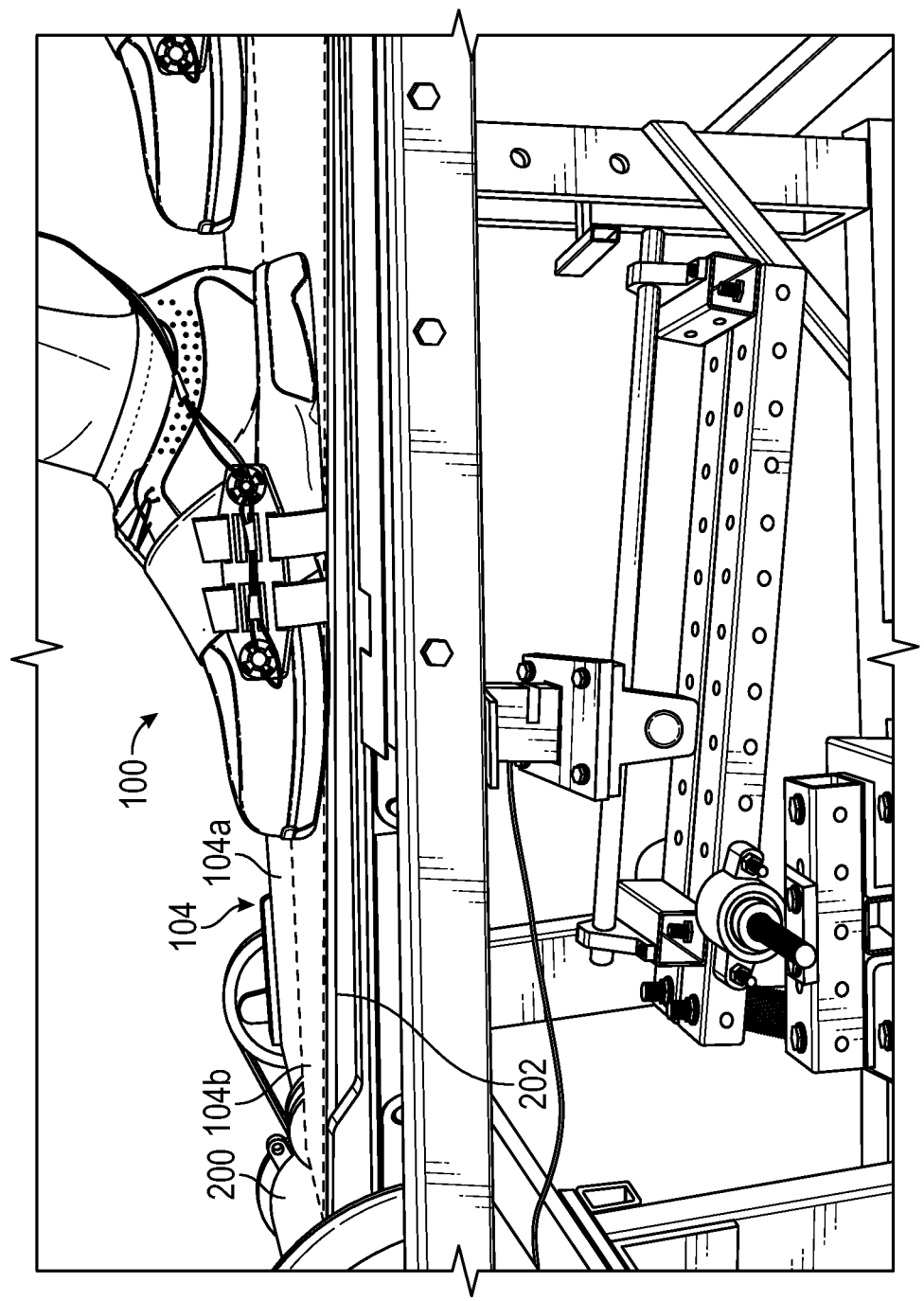

SYSTEMS AND METHODS FOR GAIT REHABILITATION USING MECHANICAL PERTURBATIONS

CROSS REFERENCE TO RELATED APPLICATIONS

This is a non-provisional application that claims benefit to U.S. provisional application Ser. No. 62/105,473 filed on Jan. 20, 2015, and is also a continuation-in-part application that claims benefit to PCT Application Ser. No. PCT/US2014/062534 filed on Oct. 28, 2014, which claims benefit to U.S. provisional application Ser. No. 61/896,509, filed on Oct. 28, 2013, and are herein incorporated by reference in their entirety.

FIELD

The present document relates to gait rehabilitation, and in particular to robotic interventions which take advantage of the mechanisms of inter-limb coordination using mechanical perturbations on the unimpaired leg to provide therapy to the impaired leg.

BACKGROUND

Stroke is a common health problem throughout the world with 795,000 new strokes occurring each year in the United States alone. Nearly 90% of stroke survivors require therapy, but the majority of patients only achieve poor functional outcome five years after the onset of stroke. Robot-assisted therapy has been proposed as an alternative approach to conventional physiotherapy because robots can easily facilitate the key behavioral signals that drive neural plasticity, which is the basic mechanism underlying improvement in functional outcome after stroke.

A variety of robotic rehabilitation devices have been developed in the last several years for gait therapy. These include the Lokomat, the Gait Trainer, and other devices. However, there have been conflicting results from recent studies about the effectiveness of these devices. Some studies report that, when compared to conventional therapy, robotic rehabilitation achieves greater functional outcome, while others indicate less improvement. Therefore, there is no clear evidence that robotic gait training is superior to conventional physiotherapy for either chronic or sub-acute stoke patients at the present time.

An alternative approach to robotic interventions in gait therapy has been proposed which takes advantage of mechanisms of inter-leg coordination. Considering the cyclic coordination between limbs in human walking, it is hypothesized that there is a mechanism of inter-limb coordination still intact after a hemiplegic stroke that may be utilized to regain functionality of the impaired leg. Utilizing the function of the unimpaired leg to provide therapy to the impaired leg provides several advantages over current rehabilitation protocols. One of the most significant advantages is the safety of the patient, since there is no direct manipulation of the paretic leg. Current robotic rehabilitation devices physically interact and manipulate the paretic leg. Moreover, stimulating a mechanism that is still fully functional may elicit greater functional outcome than in stimulating the impaired mechanism.

However, the sensorimotor control mechanisms of inter-leg coordination are currently not well understood. Various platforms and protocols have been used to investigate bilateral reflex mechanisms during different phases of the gait cycle, with the majority of the experimental protocols focusing on over-ground walking and dropping of the supportive surfaces at distinct gait phases. During posture maintenance, experiments including powerful unilateral displacement of one leg produced bilateral responses both in adults and in healthy human infants. In addition, disturbances in the load feedback as well as the length of specific muscles during walking have been associated with evoked muscular activations of the unperturbed leg. One significant limitation of the previous studies is that the perturbations induced by the previous experiments almost exclusively focus on dropping the walking surface, which causes a disruption in both force and kinematic feedback. When the walking surface is dropped, the ankle kinematics become perturbed in addition to the force feedback that is lost when the foot loses contact with the walking surface. These types of perturbations do not provide any separation of those two feedback mechanisms, and do not allow further in-depth investigation of the role of force and kinematic feedback in gait. In order to answer important questions on inter-leg coordination and sensorimotor control, it is desirable, therefore, to differentiate force and kinematic feedback. Adjustment of the surface stiffness is a unique way to achieve this differentiation, since stepping on a low stiffness platform does not disrupt force feedback (load force remains the same), but affects kinematics.

Moreover, all of the previous studies have failed to separate the mechanisms of gait from those of body weight support and balance. Moreover, most experimental protocols do not consider balance support. As a result, mechanical perturbations and sudden load changes would have likely triggered mechanisms related to body balance and posture. In fact, the latter leads to the activation of inter-limb mechanisms and therefore explains bilateral leg responses. However, little is known whether this effect is exclusively caused by the mechanisms required for body stabilization and balance maintenance, or if it is also brought about from inter-limb coordination and mechanisms of gait. This gap prevents us from fully understanding sensorimotor control of gait, and consequently from engineering effective rehabilitation protocols.

DETAILED DESCRIPTION OF THE DRAWINGS

The instant patent or application file contains at least one drawing executed in color. Copies of this patent or patent application publication with color drawing(s) will be provided by the Office upon request and payment of the necessary fee.

FIG. 10 is a picture that illustrates the downward deflection of one belt relative to another belt of the split-belt treadmill.

Figure 1:
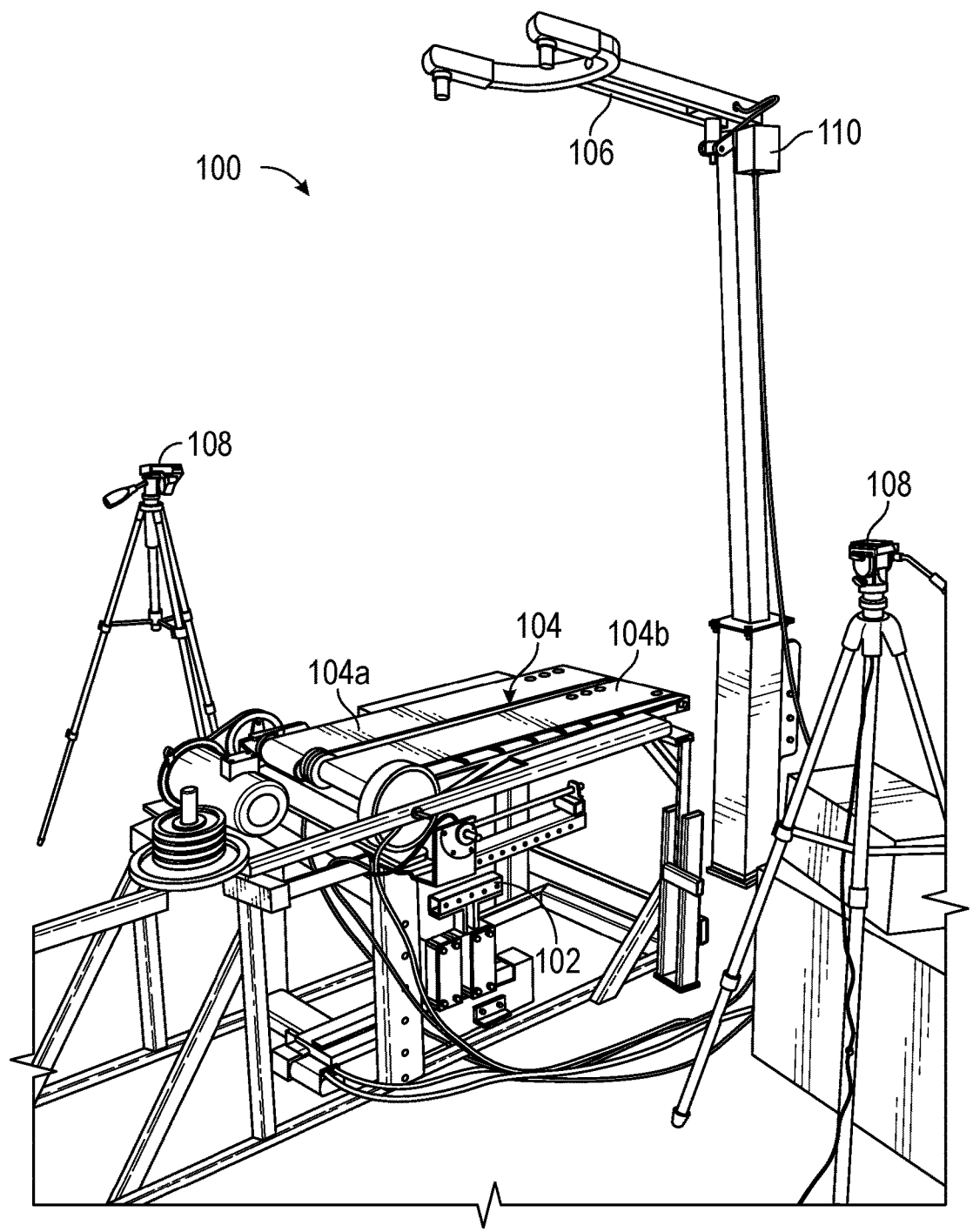
FIG. 1 is a picture of one embodiment of the Variable Stiffness Treadmill (VST) system illustrating the variable stiffness mechanism, split-belt treadmill, harness-based body-weight support, load cells, and motion capture system.

Corresponding reference characters indicate corresponding elements among the view of the drawings. The headings used in the figures do not limit the scope of the claims.

DETAILED DESCRIPTION

Referring to the drawings, various embodiments of a Variable Stiffness Treadmill (VST) system for gait rehabilitation using mechanical perturbations are illustrated and generally indicated as 100 in FIGS. 1-10. The various methods and systems of the VST system 100 are discussed below.

The investigation of the effect of unilateral stiffness perturbations on the contralateral leg was performed using the VST system 100 shown in FIG. 1. The VST system 100 provides a unique platform for proper investigation of inter-leg coordination mechanisms by combining a variety of components into one unique system. The major components of the VST system 100 include a variable stiffness mechanism 102, a split-belt treadmill 104, a custom-built body weight support 106, and a motion capture system 108. Each component will be discussed below.

1) Variable Stiffness Mechanism 102: Stiffness perturbations were chosen for investigating inter-leg coordination because of the inherent ability to differentiate force and kinematic feedback. Adjustment of the surface stiffness by a processor in operative communication with the variable stiffness mechanism provides a unique way to achieve this differentiation during walking because the force exerted by the walker's foot on the split-belt treadmill 104 remains the same independent of the stiffness of the treadmill surface. Since this force remains the same, a change in stiffness by the variable stiffness mechanism 102 will cause a displacement (i.e. kinematic perturbation).

Figure 2:
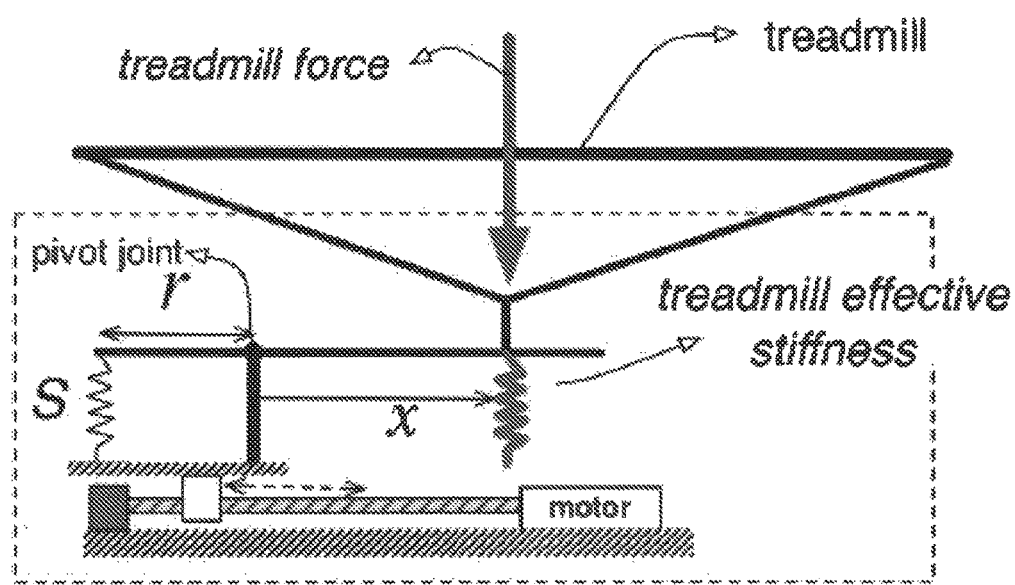
FIG. 2 is a conceptual diagram of the variable stiffness mechanism.

In its most simplified form, in some embodiments the variable stiffness mechanism 102 may be a spring-loaded lever mounted on a translational track, as shown in FIGS. 1 and 2. The effective stiffness of the split-belt treadmill 104, located at a distance x from the pivot joint, is dependent on the coefficient of stiffness S of the linear spring and the moment arm through which it exerts a force. By design, S and r remain constant, therefore, the effective stiffness of the split-belt treadmill 104 can be controlled by changing the distance x. In the VST system 100, the distance x is controlled by placing the mechanism assembly of the VST system 100 onto the carriage of a high-capacity linear track, for example a Thomson Linear (Part Number: 2RE16-150537), which is controlled by a high-precision drive, for example a Kollmorgen (Part Number: AKD-P00606-NAEC-0000). The resolution of achievable displacement of the linear track is 0.01 mm. The VST system 100 can change the surface stiffness from infinite (non-compliant walking surface) to 62 N/m (extremely low stiffness) in 0.13 seconds. The VST system 100 can also reach any belt stiffness between minimum and maximum belt stiffness at a minimal incremental value of 0.038 N/m. Therefore, the VST system 100 can create quick, high resolution stiffness perturbations of nearly any magnitude which leads to consistent, repeatable, and unanticipated stiffness perturbations that are useful for altering kinematic feedback.

2) Split-belt treadmill 104: The VST system 100 employs a split-belt treadmill having a first belt 104A and a second belt 104B to allow each individual belt 104A and 104B to deflect different amounts. In some embodiments, the treadmill belts 104A and 104B are supported at 70 cm above the floor on a frame of steel tubing that permits each belt to independently deflect the axis 200 of either the first belt 104A and 104B downward to between a minimum angle of 1 degree to a maximum angle of 30 degrees from the horizontal axis 202 of the split belt treadmill 104 as shown in FIG. 10. This will allow one leg of an individual to experience low stiffness perturbations while the other leg of the individual remains supported by a rigid surface. The split belt treadmill B is shown in FIG. 1.

3) Body weight support 106: Separate from the treadmill structure, in some embodiments there may be a custom-built body weight support 106, for example a body weight support 106 designed by LiteGait. By adjusting the height of the body weight support 106, full or partial body-weight support may be selected. This is an important capability to reduce activation of body stabilization and balance maintenance mechanisms. In addition, the body weight support 106 increases safety and extends the capabilities of the VST system 100 to stroke patients and other individuals with decreased mobility and stability. In some embodiments, two load cells 110 may be attached on the harnesses (not shown) of the body weight support 106 to measure the subject's weight supported by the VST system 100 from each side. The body weight support 106 and load cells 110 are shown in FIG. 1.

4) Motion capture system 108: Another important component of the VST system 100 is a low-cost and portable motion capture system 108. In some embodiments, the motion capture system E may include a pair of infrared camera, for example infrared cameras manufactured by Code Laboratories Inc. (Model: DUO MINI LX), and infrared LEDs, for example infrared LEDs manufactured by Super Bright LEDs Inc. (Model: IR-1WS-850) The motion capture is important for tracking the location of the subject's foot in order to maintain the desired stiffness underneath the walker, and for precise timing of stiffness perturbations within the gait cycle of the individual. The motion capture system 108 was also used for recording lower limb joint angles throughout the gait cycle of the individual. The two cameras for tracking the two legs of the individual are shown in FIG. 1.

Experimental Protocol and Data Analysis

Figure 3:
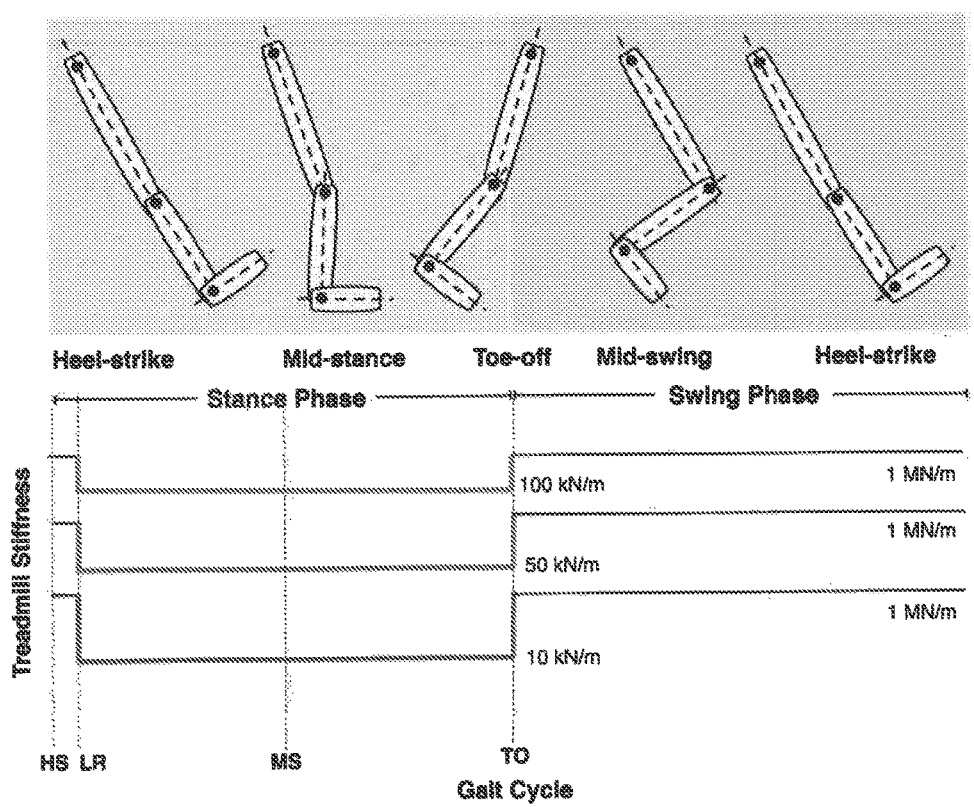
FIG. 3 is a simplified illustration showing the timing and magnitude of unilateral perturbations.

In order to investigate inter-leg coordination when body balance is not disturbed, the response of the contralateral (unperturbed) leg to unilateral stiffness perturbations while supplying the subject with approximately 30% body weight support was investigated. Five healthy subjects [age 25±5.4 years, weight 190±35 lbs] walked on the split-belt treadmill 104 at a speed of 0.60 m/s for at least 200 gait cycles. The right treadmill belt 104A (FIG. 1) was not allowed to deflect for the duration of the experiment thus preventing any direct perturbation of the right leg of the individual. The surface of the left treadmill belt 104B (FIG. 9) underneath the left leg was commanded to maintain a stiffness of 1 M N/m by the variable stiffness mechanism 102, which is considered to be rigid, for 30 gait cycles at the beginning of the experiment. Then, after a random number n of steps, the stiffness was immediately dropped to one of three values: 10, 50 or 100 kN/m. The low stiffness perturbation began shortly after heel strike (approximately 130 ms) of the individual and lasted for the duration of the left leg stance phase after which the stiffness was commanded back to 1 M N/m for the next n number of steps. A graphical representation of the timing and magnitude of the stiffness perturbations is shown in FIG. 3. An average of 17±2.3 perturbations at each stiffness level was experienced by all individuals.

Kinematic data for both legs was obtained at 140 Hz using the infrared cameras of the motion capture system 108 that tracked twelve (six on each leg) infrared LEDs placed as pairs on the thigh, shank, and foot of an individual. Informed consent from the individual was obtained at the time of the experiment, and the experimental protocol was approved by the Arizona State University Institutional Review Board (IRB ID#: STUDY00001001).

The muscle activity of the unperturbed leg of the individual was obtained using surface electromyography (EMG) via a wireless surface EMG system (Delsys, Trigno Wireless EMG) and recorded at 2000 Hz. Electrodes were placed on the tibialis anterior (TA) and soleous (SOL) of the right leg of the individual. After computing the EMG linear envelope, the data was normalized to the maximum value of that EMG signal. The EMG data corresponding to the gait cycles of walking on the rigid surface by the individual and the cycles pertaining to the three perturbations were found and normalized temporally to percent gait cycle in order to eliminate discrepancies due to natural variations in gait patterns (i.e. stride length, cycle time, etc). The first 30 gait cycles and the cycles in between perturbations at infinite stiffness (except for two cycles following a perturbation to eliminate any residual effects from the perturbation) are included in the unperturbed (i.e. "rigid") data set. This results in normalized EMG signals as a function of percent gait cycle, where 0% corresponds to the heel strike of the left leg.

Bilateral Response

Figure 4:
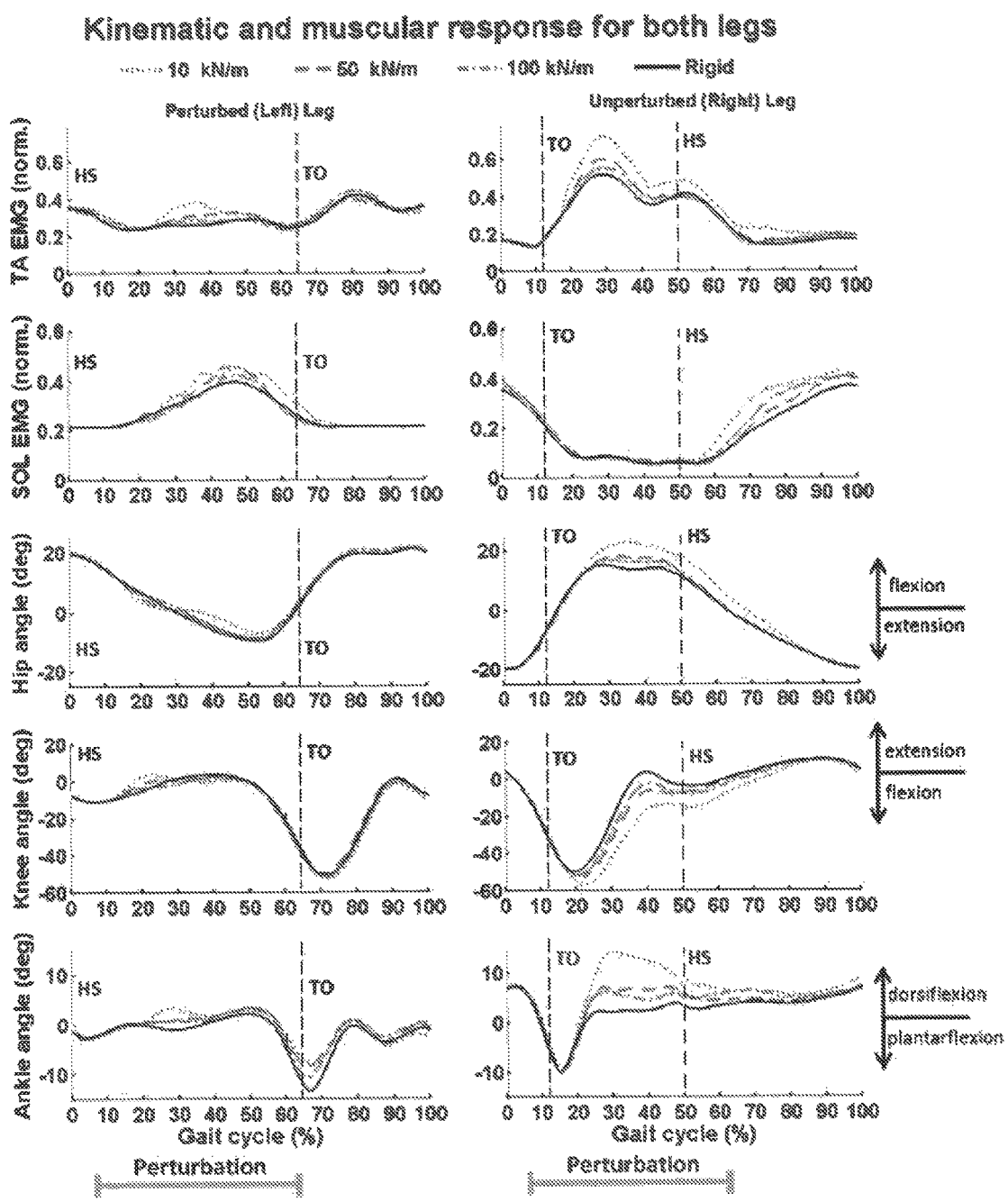
FIG. 4 are graphs showing the averaged muscle activity and joint kinematics of the perturbed (left) and unperturbed (right) legs for a representative subject.

The kinematic and muscular response to unilateral low stiffness perturbations for a representative individual is shown in FIG. 4. The normalized EMG amplitude for the TA and SOL, along with the hip flexion-extension, knee flexion-extension and dorsi-plantar flexion (mean and standard deviation) for all gait cycles pertaining to each surface stiffness is shown for both the perturbed (left) leg and unperturbed (right) leg. The data was plotted as a function of the gait cycle percentage, where heel-strike and toe-off of each leg are indicated on FIG. 4 as HS and TO, respectively. Both the muscular and kinematic profiles of walking on a rigid surface resemble that of what would be expected for normal human gait, therefore VST system 100 and experimental protocol did not alter normal gait patterns.

Although the left leg was directly perturbed through the left treadmill B2 stiffness change, the focus is to understand inter-leg coordination by investigating the response of the unperturbed leg to the stiffness perturbations. Therefore, the analyses for the rest of this disclosure will be focused on the effects of the perturbation on the contralateral leg response. Moreover, we have shown that the ipsilateral leg kinematics are significantly affected by the stiffness perturbation, thus a comparison between the perturbed and unperturbed gait cycle is redundant and beyond the scope of the present experiment.

The experimental data of the response of the unperturbed leg for all tested individuals revealed three important trends. These are: 1) a systematic change in joint angles, 2) a systematic increase in muscle activity and 3) a delayed response that is consistent across all of the tested individuals. The results demonstrating each of these trends is presented below.

1) Altered contralateral kinematics: As shown in FIG. 4 (bottom right-hand side), low-stiffness perturbations to the left leg evoked systematic changes in the kinematics of the right leg. The change in joint angles is proportional to the magnitude of the stiffness perturbation. These changes are seen beginning at approx. 20% of the gait cycle and then converge back to the normal walking pattern at around 80% of the gait cycle. The converging of the kinematic profiles of all stiffness levels before the end of the cycle indicates that the effect of the perturbation does not endure past the end of the gait cycle.

Figure 5:
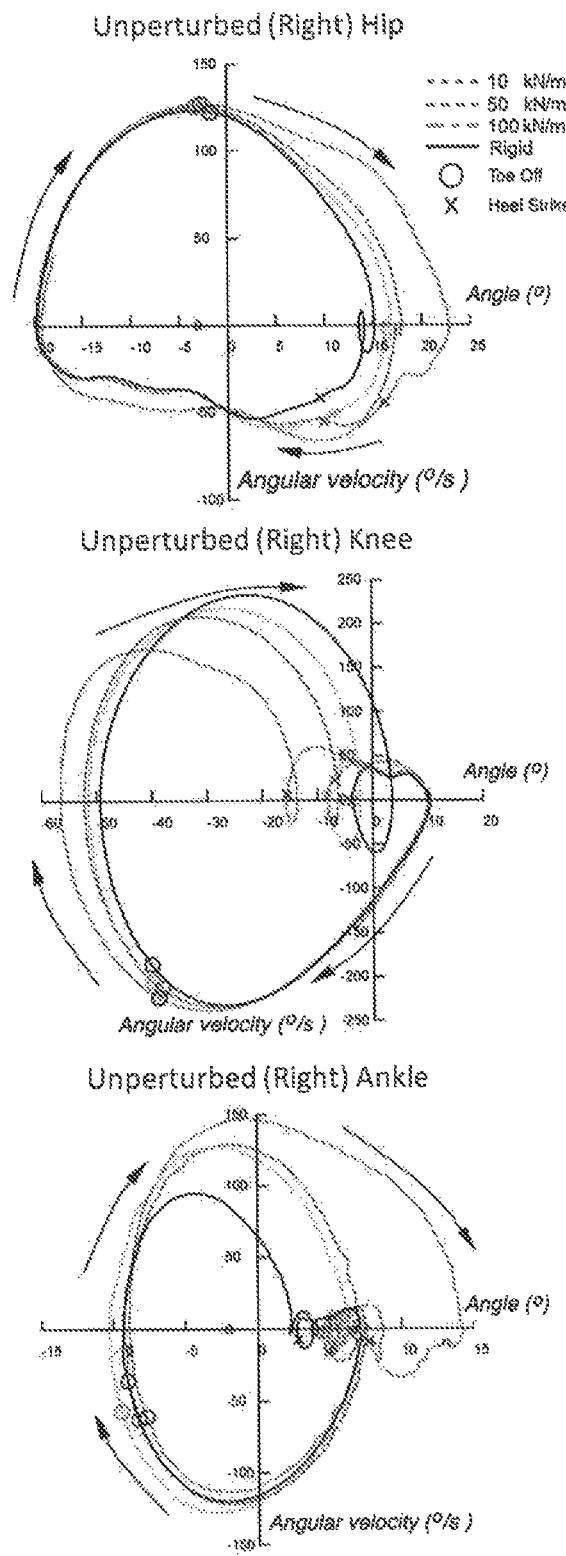
FIG. 5 are graphs illustrating the kinematic response of the unperturbed leg represented in phase space, wherein the mean angular velocity as a function of angular position is plotted for all stiffness levels.

The kinematics of the right leg was also represented in phase space (angular position vs. angular velocity). This space offers a better understanding of the behavior of a periodic system after a perturbation, and allows the analysis of the stability and robustness of the system in general. Angular velocities for all three joints that were investigated were computed by differentiating the angular position data, after applying a low-pass filter (Butterworth filter, 2nd order, cut-off frequency of 14 Hz). The phase plots of each of the three joints of the right leg are shown in FIG. 5. The toe-off and heel-strike for each of the four stiffness levels are shown. The data shown in the figure and the definition of the positive angles are identical to that of FIG. 4.

In addition to confirming the systematic increase in joint angles, the phase plots also reveal systematic changes in angular velocities of the knee and ankle joints. As the magnitude of the stiffness perturbation decreases there is decreased angular velocity of the knee joint and increased angular velocity of the ankle joint. No significant change in angular velocity of the hip joint was observed.

2) Evoked contralateral muscle activity: As shown in FIG. 4 (top right-hand side), low-stiffness perturbations to the left leg evoked muscle activity in the right leg that increased systematically with decreased stiffness. This is seen in the TA most prominently between toe-off and heel-strike (i.e. swing phase), and after heel-strike (i.e. stance phase) in the SOL. As the magnitude of the perturbation increases (i.e. lower stiffness values), there is a proportional increase in TA and SOL activity.

3) Consistent latency: Also of importance is a consistent latency across subjects from the onset of the perturbation to when increased TA activity, and altered kinematics, is seen. The normalized TA EMG (mean and standard deviation) as a function of percent gait cycle, with an indication of the delayed response, for two subjects is shown in FIG. 6.

Figure 6:
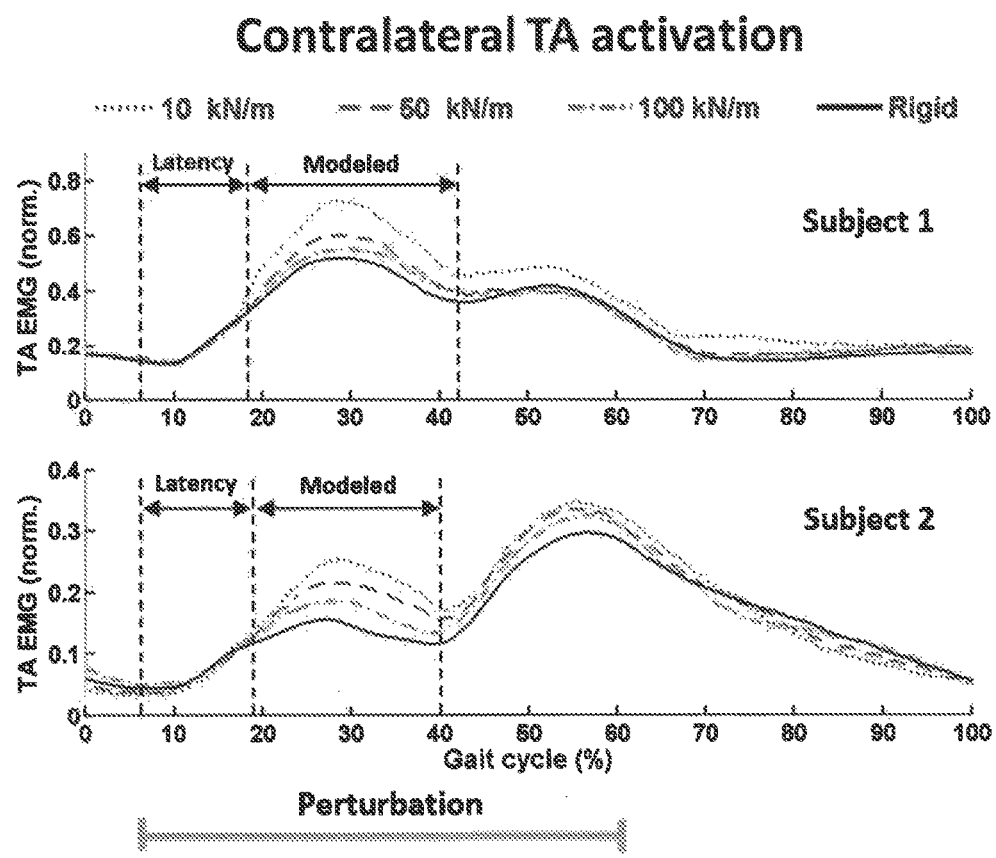
FIG. 6 are graphs illustrating the averaged tibialis anterior (TA) muscle activity for gait cycles at each of the four surface stiffness levels for two different subjects with the mean (dark lines) and the standard deviation (lightly shaded areas) values being shown along with an indication of the timing of the perturbation.

Referring to FIG. 6, the amplitude of muscle activity of all profiles is very similar from the beginning until approx. 18% of the gait cycle where they begin to diverge. The timing of the divergence was consistent across all subjects: mean 18.28%, standard deviation (SD) 0.72% gait cycle. The low stiffness perturbation began approximately 130 ms after heel strike of the left leg which corresponds to 8.0% [SD 0.8%] of the gait cycle. The latency was calculated from the beginning of the perturbation until the mean of the 10 N/m stiffness profile was greater than 1 standard deviation of the EMG activity for walking on a rigid surface. The latency averaged across all subjects resulted in a mean of 171 ms [SD 31 ms].

Mathematical Model

While many studies have investigated and described the kinematic and euromuscular effect of sensory perturbations on human gait, there does not appear to be any model, or mathematical equation, that relates the sensory input (i.e. perturbation) to the noticed effect. Such a model would be desirable for predicting the effects of sensory stimuli. In order to achieve this desired predictive capability a single-input single-output linear model was created that relates the magnitude of the stiffness perturbation to the evoked TA activity.

The output (i.e. evoked TA activity) was found by subtracting the mean EMG activity of all unperturbed cycles from each of the EMG cycles for each stiffness level. The data were then reduced to only focus on the section from the end of the delay (approx. 18% of the gait cycle) to the local minimum between the two local maximums of TA activity (approx. 41% of the gait cycle), as shown in FIG. 6. This section of data was chosen because of the interest in the TA increase during swing phase, the section of the gait cycle where a decreased dorsiflexion motion, termed drop-foot, is usually present in impaired human gait. The data for all gait cycles was then through a low-pass filter because of the interest in modeling the general trend of evoked muscle activity, as opposed to matching a high frequency EMG signal. The input used (i.e. the magnitude of the stiffness perturbation) was a constant step input with its magnitude proportional to the maximum evoked muscle activity.

System identification techniques were used to relate the measured EMG activity (model output) to the stiffness perturbation magnitude (input). A variety of model orders and types (both linear and nonlinear) were investigated as options to create a black box model. Eighty percent (80%) of all data-cycles were randomly selected for fitting the models. The resulted models were then tested against the remaining 20% of the data as validation. Expectation maximization (EM) algorithms were used for fitting the model, implemented in the System Identification Toolbox in MATLAB. Based on the normalized root mean square error between the model prediction and validation data, and the complexity of the model, a second order linear model was selected. The prediction of the model was compared to the validation data shown in FIG. 7 for a representative subject for each level of stiffness perturbation.

Figure 7:
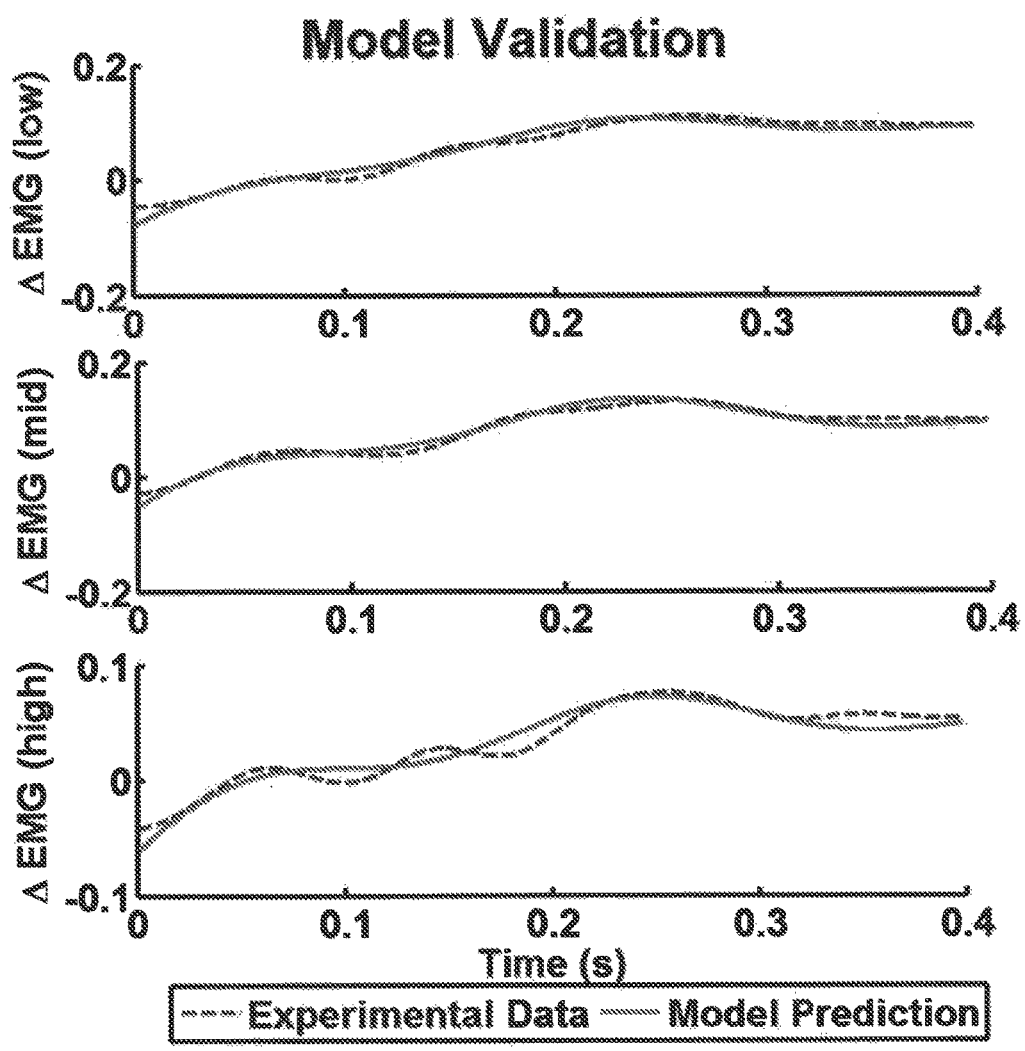
FIG. 7 are graphs showing evoked TA muscle activity versus experimental data for three perturbed stiffness values.

As shown in FIG. 7, the model accurately matches the trend of the validation data for each level of perturbed stiffness. The correlation coefficient between the model prediction and experimental data was 0.98, 0.97, and 0.94 for the perturbation stiffness levels of low, mid, and high, respectively. This successfully achieves the goal of creating a mathematical relationship between the input of a stiffness level and the evoked TA activity. The model, expressed in transfer function form, for a representative subject is shown below:

$$\frac{Y(z)}{U(z)} = \frac{0.006483 - 0.006483z^{-1}}{1 - 1.999z^{-1} + 0.9989z^{-2}} \quad (1)$$

where Y(z) is evoked TA activity (model output) and U(z) is the perturbed stiffness magnitude (model input). The model was consistent across subjects as shown by the poles and zeros of the transfer function for all subjects that participated, as listed in Table I.

TABLE I

Poles and Zeros of Fitted Models

| Subject | Poles | Zero |
|---|---|---|
| 1 | 0.9994∠ ± 0.05° | 1.0000 |
| 2 | 0.9993∠ ± 0.16° | 1.0015 |
| 3 | 0.9993∠ ± 0.05° | 1.0000 |
| 4 | 0.9991∠ ± 0.13° | 0.9989 |
| 5 | 0.9998∠ ± 0.08° | 1.0000 |

Contralateral Response

The results of this analysis confirm the hypothesis that unilateral stiffness (i.e. kinematic) perturbations can evoke a response of the contralateral leg when balance mechanisms are not involved. This suggests the existence of a mechanism of inter-leg coordination that is separate from the mechanisms related to balance and posture.

Moreover, the repeatability (consistency across subjects) and scalability (systematic increase in EMG activity and kinematic response with decreasing stiffness) suggests that walking surface stiffness is a significant stimulus in gait. As mentioned previously, stiffness control provides a unique way to differentiate force and kinematic feedback because the force exerted by the individual's foot on the treadmill remains the same so a change in stiffness will cause a displacement of the foot, without altering load feedback. While several studies have investigated the effect of length and load feedback on gait, the surface stiffness that is utilized in this study is a unique way to ensure isolation of one sensory modality.

The novel application of stiffness perturbations disclosed herein resulted in a systematic increase in muscle activity of both the TA and SOL muscles. Moreover, increased TA activity in the unperturbed leg is seen most profoundly in swing phase. This is an exciting result from a functional point of view since this can provide significant solutions to the problem of drop-foot that most impaired walking individuals suffer from, and is the leading cause of after-stroke falls. The tibialis anterior evoked activation can play a significant role in avoiding drop-foot in swing phase because it is the primary muscle creating dorsiflexion (toe-up motion). The fact that the induced perturbations can evoke the necessary ankle dorsiflexion (as observed in the kinematic response seen in FIGS. 4 and 5) to counteract drop-foot indicates that surface stiffness may play a significant role in robotic gait rehabilitation.

In addition to all of the above, the evoked responses were significantly delayed from the onset of the perturbation (delay>150 ms), which supports the idea of supraspinal pathways regulating inter-leg coordination. A delay of this duration corresponds to a transcortical reflex mechanism. Therefore, the results suggest that supraspinal circuitry is involved in the response to sudden low stiffness perturbations.

Figure 8:
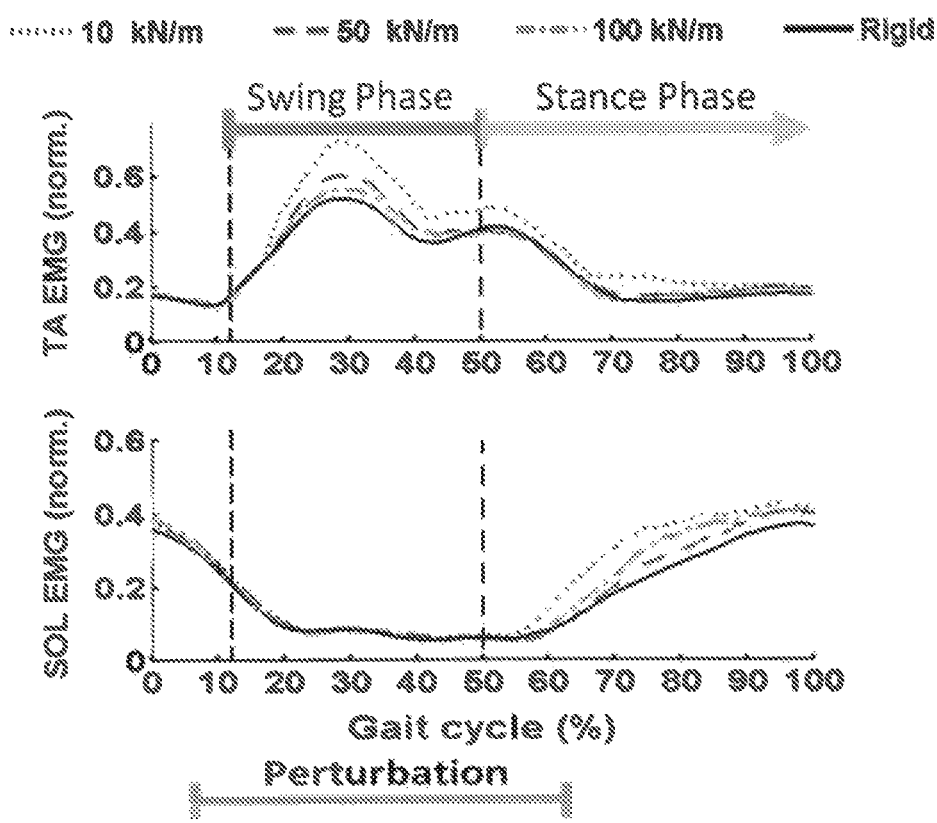
FIG. 8 are graphs illustrating averaged TA and soleous (SOL) muscle activity for gait cycles at each of the four surface stiffness levels for a representative subject with mean (darker lines) and standard deviation (lightly shaded areas) values are shown.

Moreover, the timing of evoked muscle activity with the gait cycle indicates that the brain may be involved in adjusting the gain of system. As shown in FIG. 8, the systematic increase of muscle activity only occurs when the muscle is normally active. More specifically, even though the perturbation occurs from 8% to 60% of the gait cycle, evoked muscle activity of the SOL is not seen until the end of the perturbation when the stance phase begins which is when the SOL is active in normal walking. This pattern of activation is also seen in the TA during the swing phase and beginning of the stance phase. This suggests that the brain modifies the amplitude of neuromuscular response to sensory stimuli but does not initiate activation of the muscles in gait. This is consistent with the theory that central pattern generators located in the spinal cord are responsible for generating basic gait motor patterns through cyclical flexion and extension of the joints, while the brain modulates the basic gait patterns with descending inputs.

From a clinical perspective, the results of this study can be disruptive since it suggests that muscular activity in the contralateral TA can be evoked via the cerebral cortex by altering the surface stiffness below the ipsilateral leg. A stroke results from lesions in the brain and can cause functional impairment in a variety of motor tasks, including gait. A main deficiency in stroke survivors is insufficient TA activity in the swing phase which results in a decreased dorsiflexion. The results presented above provide indications that by manipulating the non-paretic leg in stroke patients, the muscle activation in the TA of the paretic leg may be evoked through supra-spinal inter-leg coordination mechanisms. While other studies have stimulated the impaired TA via functional electric stimulation to improve functional outcome, this technique by-passes the brain which is the location of the root cause of the gait impairment created by stoke. On the other hand, our results suggest an alternative approach to create desired TA activity by exploiting existing supra-spinal neural circuits via regulation of the stiffness of the walking surface. While the results presented in this disclosure are with healthy subjects, it provides indications that the evoked TA activity can decrease dropfoot and perhaps facilitate neural plasticity in the brain for eventual recovery of normal gait in stroke patients.

Mathematical Model

The creation of a mathematical model relating sensory input to muscle activation is the foundation for creating model-based rehabilitation protocols. The second order linear model is used to relate the magnitude of the stiffness perturbation to the evoked TA activity in the unperturbed leg during swing phase. The model is able to match the trend of evoked muscle activity and could be used for prediction purposes. In other words, if certain TA activation is desirable in gait therapy, the model can be utilized to indicate the level of stiffness perturbation necessary to evoke the desired muscle activity.

In addition, the model could be used as a metric of normal gait patterns because it was proven to be consistent across healthy subjects. This provides a quantifiable level of impairment which can be utilized in rehabilitation and as a means for assessing improvement.

Experimental Results

Figure 9:
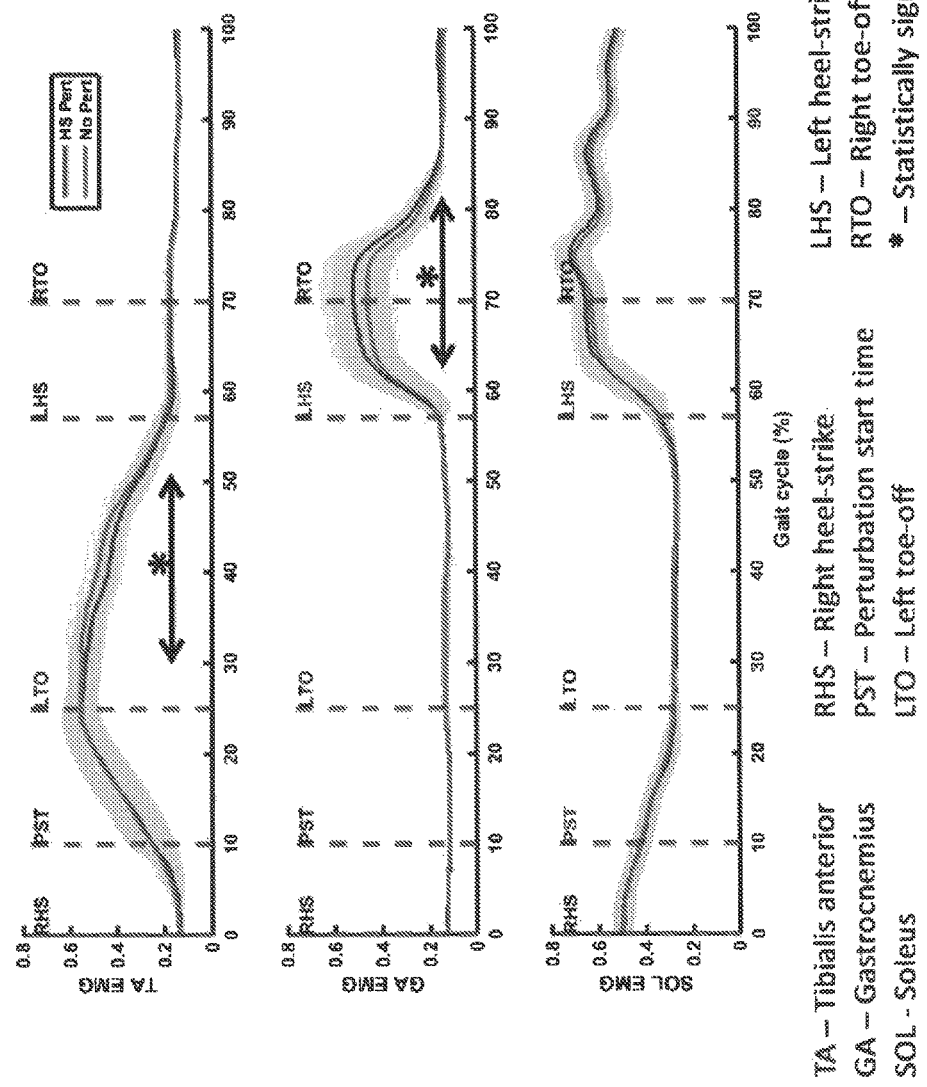
FIG. 9 illustrates graphs representing muscle activity of the unimpaired leg of a hemiplegic walker between the TA, GA and SOL muscles.

A recent patient experiment provides additional support that the proposed method would be effective for gait rehabilitation. The subject has hemi-paretic gait due to a traumatic brain injury that has affected his left leg. As the subject walked on the treadmill, the stiffness of the walking surface underneath the right leg was changed to a lower value shortly after right heel-strike during random gait cycles. Surface EMG recordings on the left (affected) leg show that muscle activity was evoked in the paretic leg due to contralateral (right treadmill) stiffness perturbations. FIG. 9 shows various graphs illustrating the EMG recordings of the tibialis anterior (TA) muscle, gastrocnemius (GA) muscle, and Soleus (SOL) muscle of the unperturbed (impaired leg) of the hemiplegic walker. The red lines show the muscle activation during normal walking and the blue lines show the response to unilateral low stiffness perturbations to the unimpaired (right) leg. Mean values (dark lines) and standard deviations (lightly shaded area) are shown as a function of the gait cycle percentage, where 0 and 100% correspond to heel-strike of the right leg. The stiffness perturbations began shortly after heel-strike of the right leg (indicated by a dashed line labeled PST) and lasted until the end of the right leg stance phase (i.e. right toe-off). The EMG recordings in the attached figure were in response to a change in stiffness from infinite (i.e. rigid surface) to 60 kN/m. A similar muscular response was seen for a stiffness change to 80 kN/m. The timing of statistically significant changes in muscle activity is indicated by a black asterisk above black arrows. The timing of important gait features are also shown in the figure with dashed lines and appropriate labels. FIG. 9 further shows that significant changes in muscle activity in the impaired leg of a hemiplegic walker can be evoked via stiffness perturbations to the opposite (unimpaired) leg.

Moreover, this experiment revealed the ability to evoke activity in different muscles of the contralateral leg depending on the relative inclination of the treadmill to the walker's foot. The VST system 100 allows the individual to walk facing in either direction on the treadmill. If the individual walks such that low-stiffness perturbations cause the treadmill belt deflection to create dorsiflexion of the perturbed ankle, then evoked activity is seen in the contralateral tibialis anterior, which is the primary muscle that creates the dorsiflexion motion. Similarly, if the individual walks such that the treadmill belt deflection causes plantarflexion of the perturbed ankle, then the evoked activity is seen in the contralateral gastrocnemius, which is responsible for plantarflexion motion. Therefore, targeted therapy can be applied to specific muscles in the impaired leg based on the direction that the individual walks.

CONCLUSIONS

This document presents results of evoking kinematic and muscular changes in the unperturbed leg of healthy subjects using stiffness perturbations to the opposite leg. The presented study provides the first evidence of unilateral stiffness perturbations having a repeatable and controllable effect on the contralateral leg. This is shown by systematic changes in joint angles and velocities, as well as the activation of the TA and SOL muscles. In addition, a latency of 171 ms from the beginning of the perturbation to the evoked response was observed for all subjects, which corresponds to neural transmission times of transcortical neural circuitry. Therefore, our results suggest the existence of supra-spinal mechanisms of inter-leg coordination that are centrally controlled.

In addition, a mathematical model is provided that accurately describes the relationship between the magnitude of a sensory perturbation and the evoked muscular change. The second order linear model presented in this paper can accurately predict the expected evoked TA activity based on a commanded surface stiffness value and lays the foundation for model-based rehabilitation protocols.

The results set the foundation for a paradigm shift of robotic interventions for gait rehabilitation. It is suggested that, in the case of healthy human subjects, manipulating sensory input of one leg can create a desired muscle activation in the other leg through mechanisms of inter-leg coordination. Future work will include testing of this hypothesis with hemiplegic stroke patients.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A method for gait rehabilitation comprising:
providing a variable stiffness treadmill comprising:
a split-belt treadmill having a first belt and a second belt;
a variable stiffness mechanism in operative association with the split-belt treadmill, wherein the variable stiffness mechanism is operative to change the stiffness of the first belt or second belt; and
a harness support configured to receive an individual for suspension above the split-belt treadmill;
positioning the individual above the variable stiffness treadmill such that a first leg of the individual is in contact with the first belt and a second leg of the individual is in contact with the second belt; and
operating the variable stiffness treadmill when the individual is walking on the first belt and second belt of the split-belt treadmill such that the variable stiffness mechanism changes the stiffness of the first belt or the second belt, respectively.

2. The method of claim 1, wherein the change in the stiffness of the first belt or the second belt generates stiffness perturbations to the first leg or the second leg, respectively, of the individual.

3. The method of claim 1, wherein the first leg of the individual is in contact with the first belt having a high level of stiffness and the second leg of the individual is in contact with the second belt having a low level of stiffness.

4. The method of claim 1, wherein the first leg of the individual is in contact with the first belt having a low level of stiffness and the second leg of the individual is in contact with the second belt having a high level of stiffness.

5. The method of claim 1, wherein the change in stiffness of the first belt or the second belt may vary in a range between 1 MN/m to 10 kN/m.

6. The method of claim 5, wherein the change in stiffness in the first belt may vary between 1 MN/m to 10 kN/m and the second belt exhibits no change in stiffness.

7. The method of claim 6, wherein the stiffness of the second belt may vary between an infinite stiffness and 62 N/m.

8. The method of claim 1, wherein the first leg of the individual is in contact with the first belt having a constant stiffness and the second leg of the individual is in contact with the second belt having a variable stiffness over time.

9. The method of claim 1, wherein either of the first belt or the second belt has a varied stiffness over time and the other of the first belt or the second belt has a constant stiffness over time.

10. The method of claim 1, further comprising:
a motion capture system in operative association with the variable stiffness treadmill for capturing the lower limb joint angles of the first leg and second leg, respectively.

11. The method of claim 1, wherein the change in stiffness of either the first belt or the second belt causes a displacement of either the first belt or the second belt.

12. The method of claim 11, wherein the displacement of either the first belt or the second belt ranges between 1 to 30 degrees, respectively, relative to a plane that extends along a longitudinal axis of the split-belt treadmill.

13. A method for gait rehabilitation comprising:
providing a variable stiffness treadmill comprising:
a split-belt treadmill having a first belt and a second belt;
a variable stiffness mechanism in operative association with the split-belt treadmill, wherein the variable stiffness mechanism is operative to change the stiffness of the split-belt treadmill; and
a harness support configured to receive an individual for suspension above the split-belt treadmill;
positioning the individual above the variable stiffness treadmill such that a paretic leg of the individual is in contact with the first belt and a non-paretic leg of the individual is in contact with the second belt; and
operating the variable stiffness treadmill when the individual is walking on the first belt and second belt of the split-belt treadmill such that the variable stiffness mechanism changes the stiffness of the second belt in contact with the non-paretic leg while maintaining a constant high stiffness of the first belt in contact with the paretic leg.

14. The method of claim 13, wherein the change in stiffness of the second belt generates stiffness perturbations to the non-paretic leg.

15. The method of claim 13, wherein the constant high stiffness of the first belt maintained by the variable stiffness mechanism is an infinite stiffness.

16. The method of claim 13, wherein changing the stiffness of the second belt in contact with the non-paretic leg invokes muscle activity in the paretic leg in contact with the first belt.

17. The method of claim 16, wherein changing the stiffness of the second belt invokes muscle activity in a soleous muscle and a gastrocnemius muscle of the paretic leg such that a foot of the paretic leg assumes a heel-up, toe-down position.

18. The method of claim 16, wherein changing the stiffness of the second belt invokes muscle activity in a tibialis anterior muscle of the paretic leg such that a foot of the paretic leg assumes a toe-up, heel-down position.

* * * * *